United States Patent [19]

Wilmet et al.

[11] Patent Number: 5,817,894
[45] Date of Patent: Oct. 6, 1998

[54] PROCESS FOR THE PREPARATION OF DIFLUOROMETHANE

[75] Inventors: Vincent Wilmet, Wavre; Francine Janssens, Vilvoorde, both of Belgium

[73] Assignee: Solvay (Société Anonyme), Brussels, Belgium

[21] Appl. No.: 922,319

[22] Filed: Sep. 3, 1997

[30] Foreign Application Priority Data

Sep. 16, 1996 [BE] Belgium .............................. 09600777

[51] Int. Cl.⁶ .................................................. C07C 17/08
[52] U.S. Cl. ........................... 570/166; 570/167; 570/168
[58] Field of Search ..................................... 570/166, 167, 570/168

[56] References Cited

U.S. PATENT DOCUMENTS

| | | |
|---|---|---|
| 2,005,711 | 6/1935 | Daudt et al. . |
| 2,749,374 | 6/1956 | Ruh et al. . |
| 2,749,375 | 6/1956 | Ruh et al. . |
| 5,495,057 | 2/1996 | Nam et al. . |
| 5,672,786 | 9/1997 | Bonniface et al. . |

FOREIGN PATENT DOCUMENTS

| | | |
|---|---|---|
| 0732314 | 9/1996 | European Pat. Off. . |
| 0767158 | 4/1997 | European Pat. Off. . |
| 0770588 | 5/1997 | European Pat. Off. . |
| 95/35271 | 12/1995 | WIPO . |
| 96/01241 | 1/1996 | WIPO . |

*Primary Examiner*—Alan Siegel
*Attorney, Agent, or Firm*—Spencer & Frank

[57] ABSTRACT

Difluoromethane is produced from dichloromethane and hydrogen fluoride by continuous reaction in a liquid medium comprising an inorganic fraction and an organic fraction, in which a content by weight of the said organic fraction in the liquid medium is maintained at less than or equal to 25% of the sum of the inorganic and organic fractions and a content by weight of dichloromethane in the liquid medium is maintained at less than or equal to 10% of the sum of the inorganic and organic fractions.

10 Claims, No Drawings

PROCESS FOR THE PREPARATION OF DIFLUOROMETHANE

The present invention relates to a process for the preparation of difluoromethane by reaction between hydrogen fluoride and dichloromethane.

U.S. Pat. Nos. 2,005,711, 2,749,374, 2,749,375 and 5,495,057 describe processes for the preparation of difluoromethane by reaction between dichloromethane and hydrogen fluoride in the liquid phase in the presence of a hydrofluorination catalyst. In these known processes, however, the catalyst generally has a tendency to rapidly become deactivated. The aim of the present invention is to provide a process for the preparation of difluoromethane by reaction between hydrogen fluoride and dichloromethane in the liquid phase which no longer exhibits the disadvantages of the abovementioned processes related to the deactivation of the catalyst.

The invention consequently relates to a process for the continuous preparation of difluoromethane, by reaction of dichloromethane with hydrogen fluoride in a liquid medium comprising an inorganic fraction and an organic fraction, which is distinguished by the maintenance in the liquid medium of a content by weight of the said organic fraction of less than or equal to 25% of the sum of the inorganic and organic fractions and of a content by weight of dichloromethane of less than or equal to 10% of the sum of the inorganic and organic fractions.

For the purposes of the present invention, inorganic fraction is understood to mean all the inorganic compounds present in the liquid medium. The inorganic fraction consequently comprises hydrogen fluoride. Advantageously, it also comprises a hydrofluorination catalyst. In addition, it can contain other inorganic compounds, in particular hydrogen chloride and water.

The organic fraction of the liquid medium in accordance with the process according to the invention is essentially composed of dichloromethane, difluoromethane, intermediate reaction products (in particular chlorofluoromethane) and possible by-products of the reaction and/or impurities of the dichloromethane.

In addition to the inorganic and organic fractions defined above, the liquid medium of the process according to the invention can optionally contain an organic solvent or additives. In a preferred embodiment of the process according to the invention, the liquid medium is composed solely of the abovementioned inorganic and organic fractions.

Subsequently, unless otherwise specified, the contents by weight will be expressed as % of the sum of the abovementioned inorganic and organic fractions.

The content by weight of organic fraction is preferably not more than 20%. In a particularly preferred way, it is not more than 15%. In general, it is not less than 1%. It is preferably not less than 2.5%. In a particularly preferred way, it is at least 5%.

The content by weight of inorganic fraction is preferably not less than 80%. In a particularly preferred way, it is not less than 85%. It generally does not a exceed 99% by weight. It preferably does not exceed 97.5% by weight. In a particularly preferred way, it does not exceed 95% by weight.

As stated above, the content by weight of dichloromethane does not exceed 10%. It preferably does not exceed 8%. It is particularly advantageous to maintain it at less than or equal to 5%. In the process according to the invention, the content by weight of dichloromethane is generally at least 0.05%. It is advantageously at least 0.5%. It is most often not less than 1%.

The content by weight of hydrogen fluoride is generally at least 5%, preferably at least 15% and, in a particularly preferred way, at least 30%. It most often does not exceed 90%. Advantageously, it does not exceed 75%. In a particularly preferred way, it does not exceed 65%.

The content by weight of hydrofluorination catalyst is usually at least 8%, preferably at least 15% and, in a particularly preferred way, at least 25%. It most often does not exceed 90%. Advantageously, it does not exceed 75%. In a particularly preferred way, it does not exceed 60%.

In the specific case where the inorganic fraction contains, in addition to hydrogen fluoride and the hydrofluorination catalyst, other inorganic compounds (for example hydrogen chloride and/or water), the total content by weight of these other inorganic compounds generally does not exceed 5%. It most often does not exceed 1%. In particular, the content by weight of hydrogen chloride generally does not exceed 2% and that of water generally does not exceed 0.5%. Advantageously, the content by weight of water is less than 0.2%.

The hydrofluorination catalyst is advantageously chosen from derivatives of metals from groups 3, 4, 5, 13, 14 and 15 of the Periodic Table of the Elements (IUPAC 1988) and their mixtures. Derivatives of metals is understood to mean the hydroxides, the oxides and the inorganic salts of these metals, and their mixtures. Use is particularly made of derivatives of titanium, niobium, tantalum, molybdenum, boron, tin and antimony. The catalyst is preferably chosen from derivatives of metals from groups 4, 14 and 15 of the Periodic Table of the Elements and more particularly from derivatives of titanium, tin and antimony. In the process according to the invention, the preferred derivatives of the metals are their salts and the latter are preferably chosen from halides and more particularly from chlorides, fluorides and chlorofluorides. Chlorides, fluorides and chlorofluorides of tin and of antimony, in particular tin tetrachloride and antimony pentachloride, are hydrofluorination catalysts which are particularly advantageous in the process according to the invention. Antimony pentachloride is very particularly recommended.

The molar ratio of the catalyst to the dichloromethane in the liquid medium is generally greater than 1. It is preferably greater than 2. Very good results were obtained in the presence of at least approximately 2.5 mol of catalyst per mole of dichloromethane. In principle, there is no upper limit to this ratio. It can, for example, reach 1000. It most often does not exceed 100.

The molar ratio of the catalyst to the hydrogen fluoride in the liquid medium can vary within wide limits. It is generally greater than 0.01. It is preferably greater than 0.02. Very good results were obtained in the presence of at least approximately 0.025 mol of catalyst per mole of hydrogen fluoride. In general, this ratio does not exceed 1.2. It most often does not exceed 0.5. Good results were obtained with a ratio not exceeding 0.1.

In the process according to the invention, hydrogen fluoride and dichloromethane, preferably in a liquid state and in a molar ratio of approximately 2, are introduced into the liquid medium. In practice, this ratio is adjusted so as to keep the composition of the liquid medium substantially constant.

The process according to the invention can be carried out within wide temperature and pressure ranges. Generally, the operation is carried out at a temperature of at least approximately 75° C. A temperature of at least approximately 90° C. is preferred. A temperature of at least approximately 100° C. is particularly preferred. Most often, depending in particular on the allowable pressure, this temperature does not exceed approximately 160° C., temperatures of less than or equal to approximately 140° C. being especially recommended. Generally, the operation is carried out at a pressure of at least approximately 2 bar. A pressure of at least approximately 10 bar is preferred. A pressure of at least approximately 15 bar is particularly preferred. This pressure most often does not exceed approximately 50 bar, pressures of less than or equal to approximately 30 bar being especially recommended.

The process according to the invention can be implemented in any type of reactor or device which is resistant to pressure and to hydrogen fluoride and which makes it possible to continuously maintain a substantially stable composition of the liquid medium. The process according to the invention is most often carried out in a reactor equipped with a device for withdrawing a gas stream, for example in a reactor surmounted by a column and a reflux condenser. This device makes it possible to continuously maintain a composition of the liquid medium in accordance with the instructions stated above, by an appropriate adjustment of the operating conditions (in particular the flow rates of the reactants entering the reactor, the temperature and the pressure in the reactor and the temperature in the condenser). In addition, a content by weight of hydrofluorination catalyst in the liquid medium of not less than 20% of the sum of the inorganic and organic fractions promotes ready removal of the organic compounds by withdrawal.

The residence time of the reactants in the reactor must be sufficient for the reaction of dichloromethane with hydrogen fluoride to take place with an acceptable yield. It can easily be determined as a function of the operating conditions used.

As the process according to the invention takes place continuously, it is understood that the proportions of the inorganic and organic fractions and the contents of the various constituents of the liquid medium reported above express stationary amounts obtained after starting the reactor.

Surprisingly, the hydrofluorination catalyst becomes deactivated much more slowly in the process according to the invention than in known processes, whereas the low content of dichloromethane in the liquid medium does not substantially affect the difluoromethane productivity.

The examples below illustrate the invention in a non-limiting way.

EXAMPLE 1

150 g of hydrogen fluoride and 145.8 g of tin tetrachloride were introduced into a 0.5 l autoclave made of Hastelloy B2 stain steel equipped with a paddle stirrer and surmounted by a jacketed condenser. The autoclave was then immersed in a thermostatically-controlled bath, maintained at a temperature of 130° C., and the pressure was adjusted to 23.5 bar. The condenser was maintained at a temperature of 45° C. The reactor was continuously supplied with liquid dichloromethane and with liquid hydrogen fluoride, in virtually stoichiometric proportions, for 200 hours. During the test, the throughputs of the dichloromethane and hydrogen fluoride flows were adjusted (between 200 and 375 mmol/h for dichloromethane), so as to stabilize the level of liquid in the reactor. The gas stream continuously exiting from the condenser was treated in a scrubber using a potassium hydroxide solution, so as to scrub out the hydrogen fluoride and the hydrogen chloride which it contained. The composition of the gas stream thus treated was then determined by in-line analysis by gas chromatography. Under operating conditions, the content of inorganic fraction in the liquid medium in the reactor was approximately 87.4% by weight and the content of organic fraction was approximately 12.6% by weight, including 4.9% by weight of dichloromethane, 5.5% by weight of chlorofluoromethane and 1.7% by weight of difluoromethane. The gas stream exiting from the scrubber contained, on average, from 75 to 80 molar % of difluoromethane, from 20 to 25 molar % of chlorofluoromethane and less than 2 molar % of dichloromethane. Overall, 99% of the dichloromethane employed was converted, including 78% into difluoromethane and 22% into chlorofluoromethane. No other product was detected. An average difluoromethane productivity of 0.3 mol per hour and per mole of catalyst was obtained. No deactivation of the catalyst was observed throughout the duration of the test. On completion of the 200 hours of reaction, the difluoromethane productivity was still at least 0.3 mol per hour and per mole of catalyst. Moreover, no corrosion of the reactor was observed.

EXAMPLE 2 (comparison)

The test of Example 1 was repeated with an initial liquid medium in the reactor composed of 150 g of hydrogen fluoride, 53 g of tin tetrachloride and 100 g of dichloromethane. After reacting for 12 hours at 115° C. under a pressure of 23.5 bar, the content of inorganic fraction in the liquid medium in the reactor was approximately 69.1% by weight and the content of organic fraction was approximately 30.9% by weight, including 20.3% by weight of dichloromethane, 10.5% by weight of chlorofluoromethane and 0.1% by weight of difluoromethane. After neutralization, the gas stream exiting from the condenser contained, on average, 76 molar % of difluoromethane, 22 molar % of chlorofluoromethane and 2 molar % of dichloromethane. An average difluoromethane productivity of 0.375 mol per hour and per mole of catalyst was obtained for 30 hours. After this period, the activity of the catalyst suddenly decreased, causing a rapid fall in the difluoromethane productivity, so that, after reacting for 40 hours, the difluoromethane productivity was virtually zero.

We claim:

1. Process for the continuous preparation of difluoromethane, by reaction of dichloromethane with hydrogen fluoride in a liquid medium comprising an inorganic fraction and an organic fraction, in which a content by weight of the said organic fraction in the liquid medium is maintained at less than or equal to 25% of the sum of the inorganic and organic fractions and a content by weight of dichloromethane in the liquid medium is maintained at less than or equal to 10% of the sum of the inorganic and organic fractions.

2. Process according to claim 1, in which the content by weight of organic fraction in the liquid medium is from 1 to 20% of the sum of the inorganic and organic fractions.

3. Process according to claim 1, in which the content by weight of organic fraction in the liquid medium is from 2.5 to 15% of the sum of the inorganic and organic fractions.

4. Process according to claim 1, in which the content by weight of dichloromethane in the liquid medium is from 0.05 to 8% of the sum of the inorganic and organic fractions.

5. Process according to claim 1, in which the content by weight of hydrogen fluoride in the liquid medium is from 5 to 90% of the sum of the inorganic and organic fractions.

6. Process according to claim 1, in which the content by weight of hydrofluorination catalyst in the liquid medium is from 8 to 90% of the sum of the inorganic and organic fractions.

7. Process according to claim 6, in which the catalyst is chosen from derivatives of titanium, tin and antimony.

8. Process according to claim 6, in which the molar ratio of the catalyst to the dichloromethane in the liquid medium is from 1 to 1000.

9. Process according to claim 6, in which the molar ratio of the catalyst to the hydrogen fluoride in the liquid medium is from 0.01 to 1.2.

10. Process according to claim 1, in which the reaction is carried out at a temperature of approximately 75° to 160° C. and at a pressure of approximately 2 to 50 bar.

* * * * *